United States Patent

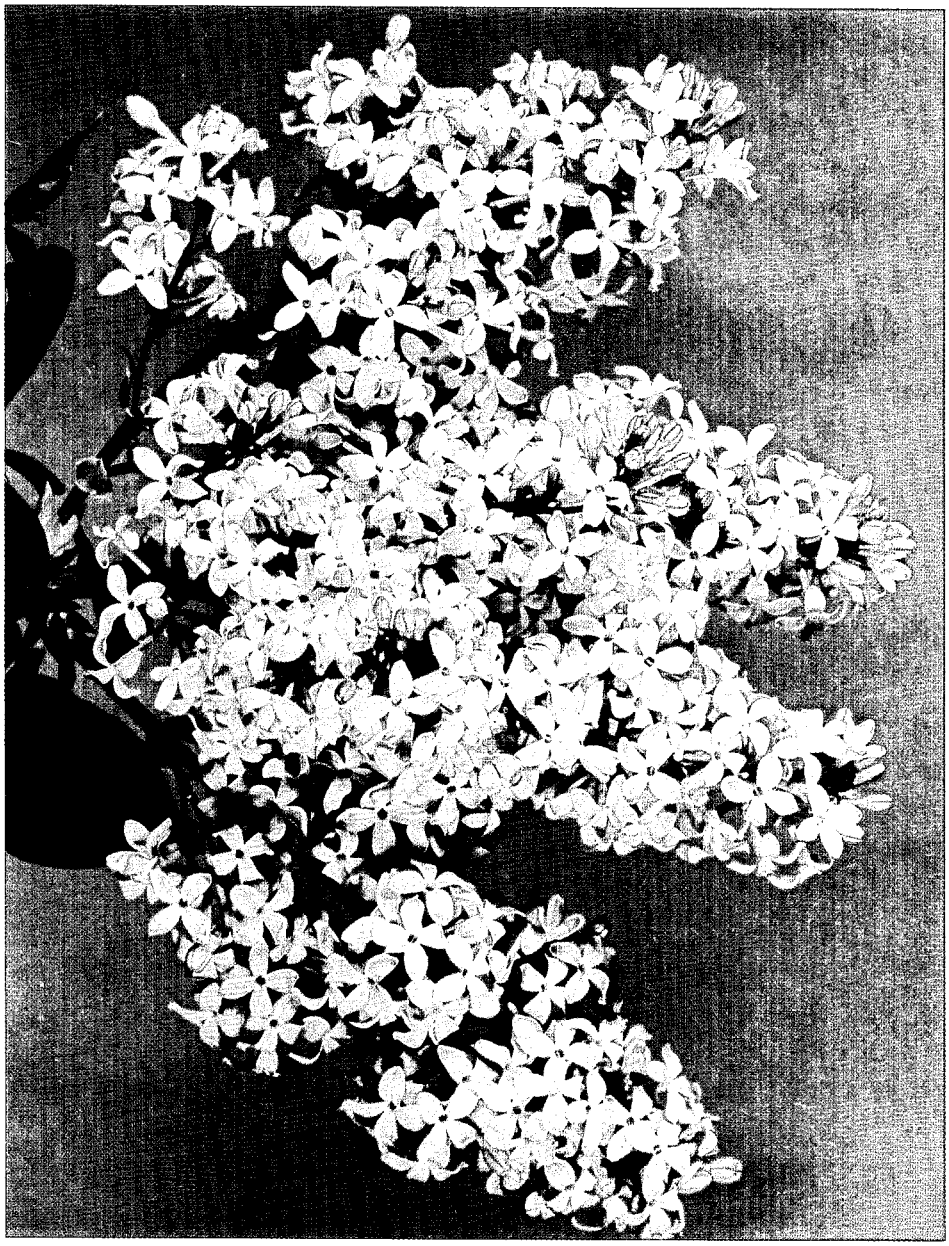

Plant Pat. 3,885
Patented May 11, 1976

3,885
LILAC PLANT

Walter E. Lammerts, Corralitos, Calif., assignor to Hines Wholesale Nurseries, Santa Ana, Calif.

Filed Mar. 24, 1975, Ser. No. 561,327
Int. Cl. AO1H *5/00*
U.S. Cl. Plt.—66 1 Claim The present invention relates to a new and distinct variety of lilac plant originated by me by crossing two unnamed and unpatented seedlings, each of which was derived from seedlings derived from various crosses I have made with seed of an unnamed and unpatented early-leafing variety identified by me in my breeding records by the identification number C112.

The primary objective in making this cross was to further and improve the objectives set forth in Plant Pat. 1,238 previously granted to me on Jan. 5, 1954. As set forth in this prior application, I had produced a lilac which would flower normally in southern California and comparable climatic areas having short and mild winters. The present invention relates to a lilac plant which requires less than normal winter-chilling required by most lilacs, including the usual eastern lilacs, and still produces normal flowering bloom clusters.

My new variety is characterized by its ability to achieve normal flowering without requiring normal winter-chilling; by its regularity and abundance of bloom consisting of very large flower clusters measuring from 7 to 10 inches in length and from 7 to 12 inches in width; and by the size of relatively large florets, at times measuring from ⅞ of an inch to 13/16 inch in diameter. Occasional flower clusters will be as large as 12 inches in both length and width.

The new variety was asexually reproduced by me on cultivated property known as Descanso Distributors at Chino, Calif. Reproduction of this new variety was made by cuttings and also by budding to ligustrum understock, and as a result established that the foregoing distinguishing characteristics come true to form and are established and transmitted through succeeding propagations.

The drawing which accompanies this petition shows a typical view of the flowers and foliage of my new lilac variety and is portrayed in color as fairly as can possibly be obtained by this method of illustration.

To facilitate identification of the important colors, I have used the color terminology of the R.H.S. Colour Chart issued by the Royal Horticultural Society of London.

Locality where grown and observed: Descanso Distributors Nursery in Chino, Calif.

Parentage: Seedling resulting from planned propagation.

*Seed parent.*—A large-petalled unpatened seedling of an unnamed early-leafing variety identified in my breeding records as C112, crossed to unnamed seedling identified in my breeding records as 42–108–4.

*Pollen parent.*—A deep pink unnamed seedling derived from seed produced by open pollination of a seedling of unpatented variety name Syringa "Buffon," identified in my breeding records as 42–109–4.

The seeds which were produced by this cross in 1950, were sown in 1951, and plants first bloomed in 1953.

Blooming habits: Early; usually from about the early part of March to mid-April in southern California. In full flower and leaf by the end of March.

THE PLANT

Form of plant: Bush.

Growth: Upright; vigorous; compact.

Branches:

New growth is in the Yellow-Green Group, Plate 145A to Plate 145B.

Mature growth is in the Greyed-Green Group, Plate 197C to plate 197D.

Foliage:

*Size.*—2 inches to 2¼ inches wide and from about 2½ inches to about 3¼ inches long.

*Quantity.*—Abundant.

*Shape.*—Ovate with an acuminate tip, and a cordate base. The leaf margin is entire.

*Venation.*—Pinnate.

*Arrangement.*—Opposite.

*Color.*—New leaves—In the Yellow-Green Group, Plate 146A to Plate 146B.

*Mature leaves.*—In the Green Group, Plate 141A to Plate 141B.

THE FLOWER

Bud: Individual florets of cluster.

*Size.*—Large.

*Form.*—Short with a flat to an elongate tip.

*Color.*—Outside is in the Red-Purple Group, Plates 70C to 70D. The opening bud is in the Red-Purple Group, Plates 70C to 70D, fading to Red-Purple Group, Plates 73C to 73D. Groupings of buds tend to have the appearance of Red-Purple Group, Plate 65B.

Bloom: Individual florets of cluster, about ⅞ of an inch, to about 13/16 inches in diameter. Florets are borne in large clusters measuring from 7 to 10 inches in length and from 7 to 12 inches in width, with occasional clusters as large as 12 inches in both length and width. Individual raceme lengths comprising the cluster range from 2 inches to 2¾ inches in length.

*Color.*—Center of the open flower starts at Red-Purple Group, Plate 68C to 68D, fading towards the tips to Red-Purple Group, Plate 65D and to almost White Group, Plate 155B.

I claim:

1. A new and distinct variety of lilac plant, substantially as herein shown and described, characterized particularly as to novelty by its relatively short and mild winter-chilling requirements, by its regular and abundant production of large flower clusters consisting of large individual florets, by its vigorous habit of plant growth, and by its abundant production of large and attractive foliage.

No references cited.

ROBERT E. BAGWILL, Primary Examiner